(12) United States Patent
Christopher

(10) Patent No.: US 7,063,088 B1
(45) Date of Patent: Jun. 20, 2006

(54) INTRAORAL ENDOTRACHEAL TUBE HOLDER AND METHOD FOR INTUBATION

(76) Inventor: Marcus Christopher, 7742 Redbird La., San Antonio, TX (US) 78240

( * ) Notice: Subject to any disclaimer, the term of this patent is extended or adjusted under 35 U.S.C. 154(b) by 0 days.

(21) Appl. No.: 11/070,482

(22) Filed: Feb. 26, 2005

(51) Int. Cl.
*A61M 16/00* (2006.01)

(52) U.S. Cl. ............... 128/207.17; 128/207.14; 128/DIG. 26

(58) Field of Classification Search ......... 128/848, 128/859, 860, 861, 200.24, 200.26, 202.27, 128/206.24, 207.14, 207.15, 207.16, 207.17, 128/207.18, 207.29, 912, DIG. 26; 604/174
See application file for complete search history.

(56) References Cited

U.S. PATENT DOCUMENTS

| | | | | |
|---|---|---|---|---|
| 3,946,742 A * | 3/1976 | Eross | ............ | 128/207.17 |
| 4,331,143 A * | 5/1982 | Foster | ............ | 128/207.17 |
| 4,906,234 A * | 3/1990 | Voychehovski | ............ | 604/79 |
| 5,894,840 A | 4/1999 | King | | |
| 5,934,276 A * | 8/1999 | Fabro et al. | ............ | 128/207.17 |
| 6,067,985 A | 5/2000 | Islava | | |
| 6,634,359 B1 * | 10/2003 | Rudy et al. | ............ | 128/207.14 |
| 6,840,238 B1 * | 1/2005 | Van Hegelsom | ............ | 128/201.22 |
| 2005/0092328 A1 * | 5/2005 | Herrick et al. | ............ | 128/207.17 |

* cited by examiner

*Primary Examiner*—Teena Mitchell
(74) *Attorney, Agent, or Firm*—Rafael V. Baca; Baca Law Firm, PLLC

(57) ABSTRACT

A tube holder assembly and method for securing an endotracheal tube to a biteline of a patient's mouth. The tube holder assembly features a tube body. A bite support assembly, coupled to the tube body, receives a tensile force and supplies a compressive force to the mouth of the patient. The bite support assembly includes a pair of substantially parallel bite walls extending outwardly from the exterior surface of the tube body. The bite walls define a bite rest therebetween for receiving a biteline of the patient's mouth and thus securing the biteline between a pair of bite walls as the bite rest applies a compressive force to the biteline.

18 Claims, 8 Drawing Sheets

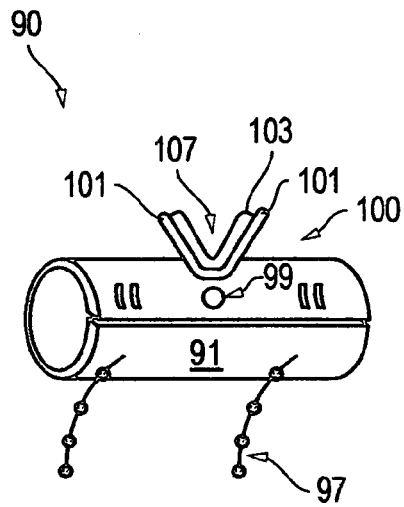
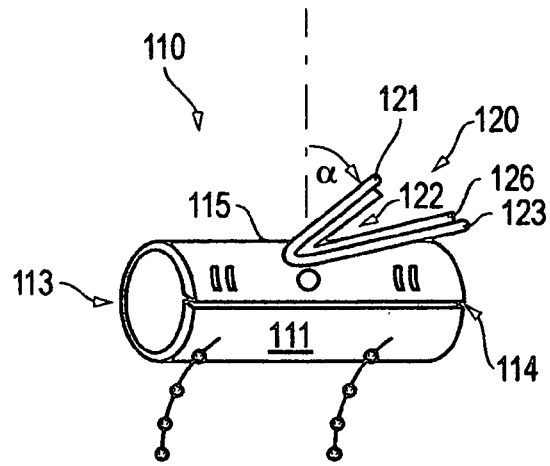
*FIG. 3*  *FIG. 4*
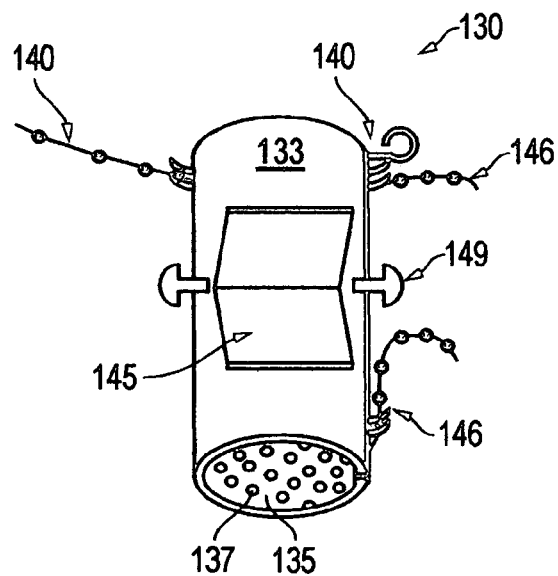
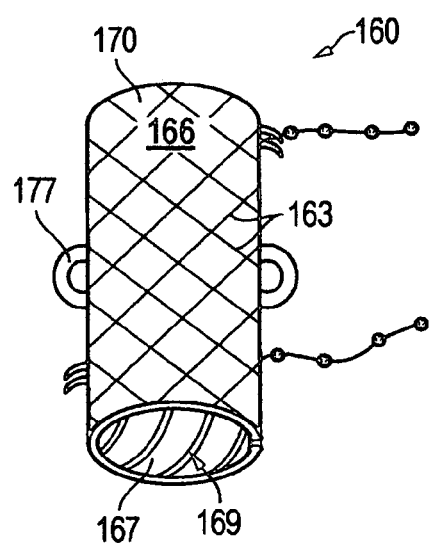
*FIG. 5*  *FIG. 6*

INTRAORAL ENDOTRACHEAL TUBE HOLDER AND METHOD FOR INTUBATION

BACKGROUND OF THE INVENTION

1. Field of the Invention

The present invention generally relates to an intraoral tube holder assembly for supporting an endotracheal tube. More particularly, but not by way of limitation, the present invention relates to a system and method for securing an endotracheal tube to a biteline of a patient's mouth wherein the system incorporates the features of both a tube holder and bite block in a single tube holder assembly.

2. Description of the Related Art

Intubation is a well known medical procedure referring to the placement of a tube in to a body orifice. Endotracheal intubation, a very common intubation procedure, directs a tube from either the mouth or the nose through the larynx to the trachea for fluid engagement therein. Most often, tracheal intubation is applied in emergency medicine especially during cardiopulmonary resuscitation, CPR; for intensive care patients under respiratory support; for protecting the airways of comatose or intoxicated patients; and for general anesthesia applications.

Often, tube holders are incorporated with endotracheal intubation procedures for supporting and maintaining the position of the endotracheal tube during a medical procedure. Many typical tube holders include a mounting plate for applying pressure to the face, such as onto the lips of the mouth, onto the cheekbone area or a combination thereof to secure the tube holder in place. Oftentimes adhesives are included with or act in conjunction with the mounting plate to enhance overall stability of current tube holders.

Unfortunately, today's tube holders create many difficulties for medical practitioners and patients alike. Many typical tube holders feature a complex array of mounting plate configurations for application to the face of the patient whereby operational setup is time consuming and laborious.

In particular, set up often needlessly involves several physicians and nurses who take turns maintaining the position of the endotracheal tube while the complicated array of mounting plates and adhesives of many typical tube holder are properly situated on to the patient by the team of medical practitioners. The application of adhesives in combination with a complex mounting plate arrangement allows very little opportunity for readjustment of the tube holder during a medical procedure as relocating mounting plates becomes cumbersome and adhesives lose their initial bonding strength.

Furthermore, the complex arrangements of many typical tube holders today often obstruct clear entry into the mouth, which is critically important for suction, inspection, maintaining the cleanliness of the endotracheal tube as well as maintaining the health of the patient's mouth during long term care. Dirt and bodily secretions such as saliva, sweat, oils from the skin, and blood delivered by the patient onto the mounting plates and associated adhesives diminish the overall operative effectiveness of a tube holder as well as the overall sterile integrity thereof. It should be added that prolonged application of pressure by the tube holders against the skin of the face could lead to trauma or ulceration from the mounting plates. Unfortunately there is no known compact device or method for operatively holding an endotracheal tube during intubation that is simple and easy to use for both the medical practitioner and patient alike.

Therefore, a need exists for a system and method for securing an endotracheal tube to a patient's mouth, simply, quickly, and without unnecessary complications to the patient's face. Many other problems and disadvantages of the prior art will become apparent to one skilled in the art after comparing such prior art with the present invention as herein described.

SUMMARY OF THE INVENTION

Aspects of the invention are found in a tube holder assembly and method for securing an endotracheal tube to a biteline of a patient's mouth. The tube holder assembly is compact, requires no adhesive support, and facilitates easy adjustment and readjustment of the endotracheal tube by a single medical practitioner.

In one aspect, the tube holder assembly features a tube body having an exterior surface, an interior surface, and a pass-through slit along the length of the tube body. Operatively, an endotracheal tube is inserted through the pass-through slit to the interior surface and is placed in direct contact about the circumference of the tube body defined by the interior surface, hereinafter referred to as "circumferential contact".

A bite tensioner mount is coupled to the tube body and receives a tensile force from a bite tensioner assembly. The bite tensioner assembly features two opposing ends having a tensioner lock at one end and anchor webbing at another end. Operatively, the tensioner lock is secured to the bite tensioner mount of the tube body whereas anchor webbing is fixed to the patient so that a tensile force is exerted along the bite tensioner assembly from the tensioner lock to the anchor webbing. Anchor webbing is advantageous for securing the bite tensioner assembly to the patient's body, especially in instances where hair, oil, skin, and dirt provide slippage at particular locations as compared with the overall surface area contact provided by the anchor webbing.

A bite support assembly, coupled to the tube body, receives a tensile force from the bite tensioner mount and supplies a compressive force to the mouth of the patient. The bite support assembly includes a pair of substantially parallel bite walls extending outwardly from the exterior surface of the tube body. The bite walls define a bite rest therebetween for receiving the biteline of a patient's mouth and thus securing the biteline between the pair of bite walls as the bite rest applies a compressive force to the biteline. Accordingly, the surface of biteline contact defined by a first bite wall, the bite rest, and an adjacent, second bite wall forms a trough-like configuration, such as either a U or V shape, for ensuring that the biteline is securely clamped therein. In one aspect, the separation between the first and second bite wall with respect to the bite rest forms a geometric angle in a range between 10° and 90°. It should be added that the term "substantially parallel" refers to the condition of being in a range from nearly parallel to exactly parallel. 'substantially parallel' refers to the condition providing one bitewall extending outwardly from the exterior surface of the tube body having a distal portion that does not intersect with a distal portion of another outwardly extending bitewall and whereby these distal portions are relatively aligned in a range from nearly parallel to exactly parallel to one another.

In one aspect, the tube holder assembly may include a peripheral fastening assembly coupled to the exterior surface of the tube body. In operation, the peripheral fastening assembly receives at least one peripheral tube thereby coupling the at least one peripheral tube to the exterior surface of the tube body. In effect, with the peripheral fastening assembly, additional tubes may be attached to the tube holder assembly during intubation such as for example a nasogastric tube, an orogastric tube, an esophogeal thermometer, and Dobhoff feeding tube.

In one aspect, a method for intubating a patient includes inserting an endotracheal tube within a tube holder assembly via a pass-through slit extending along the length of the tube body. An endotracheal tube is directed through to a desired position with respect to a patient's trachea. In one aspect, a tube holder assembly is secured to a bite line of a patient's mouth via a bite support assembly coupled to the tube body. Accordingly, the bite support assembly is compressed against the biteline of a patient. The endotracheal tube is locked in place via a slit tensioning assembly to ensure no undesired movement of the endotracheal tube with respect to the tube holder assembly. In one aspect, the tube holder assembly is anchored to the patient's head via a bite tensioner mount coupled to the tube holder assembly. Other aspects, advantages, and novel features of the present invention will become apparent from the detailed description of the present invention when considered in conjunction with the accompanying drawings.

BRIEF DESCRIPTION OF THE DRAWINGS

The present invention is illustrated by way of example and not by limitation in the accompanying figures, in which like references indicate similar elements, and in which:

FIG. 3 is an isometric view from the side illustrating one exemplary embodiment of a tube holder assembly featuring a bite support assembly;

FIG. 4 is an isometric view from the side illustrating one exemplary embodiment of a tube holder assembly featuring a bite support assembly;

FIG. 5 is an isometric view from the top illustrating one exemplary embodiment of a tube holder assembly, the tube holder assembly features an array of grip enhancers positioned about the interior surface for compression against the endotracheal tube and at least one peripheral fastening assembly for securing a respective peripheral tube such as a nasogastric tube to the exterior surface of the tube holder assembly during intubation;

FIG. 6 is an isometric view from the bottom illustrating one exemplary embodiment of a tube holder assembly, the tube holder assembly features bite grooves disposed along the exterior surface for enhanced frictional contact with the patient's mouth;

Skilled artisans appreciate that elements in the Figures are illustrated for simplicity and clarity and have not necessarily been drawn to scale. For example, the dimensions of some of the elements in the Figures may be exaggerated relative to the other elements to help improve understanding of the embodiments of the present invention.

DETAILED DESCRIPTION

For a more complete understanding of the present invention, preferred embodiments of the present invention are illustrated in the Figures. Like numerals being used to refer to like and corresponding parts of the various accompanying drawings. It is to be understood that the disclosed embodiments are merely exemplary of the invention, which may be embodied in various forms.

Figure 1:
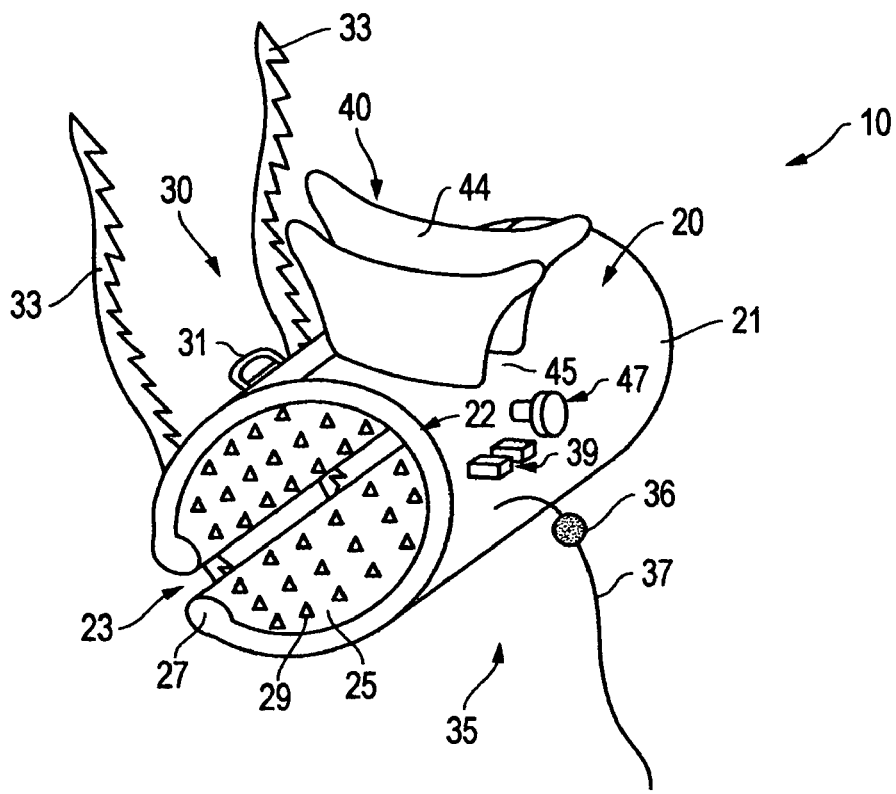
FIG. 1 is an isometric view illustrating a tube holder assembly for securing an endotracheal tube to a patient's biteline according to the present invention, the tube holder assembly includes a bite support assembly coupled to a tube body for applying a compressive force while clamped around the biteline.
Figure 7:
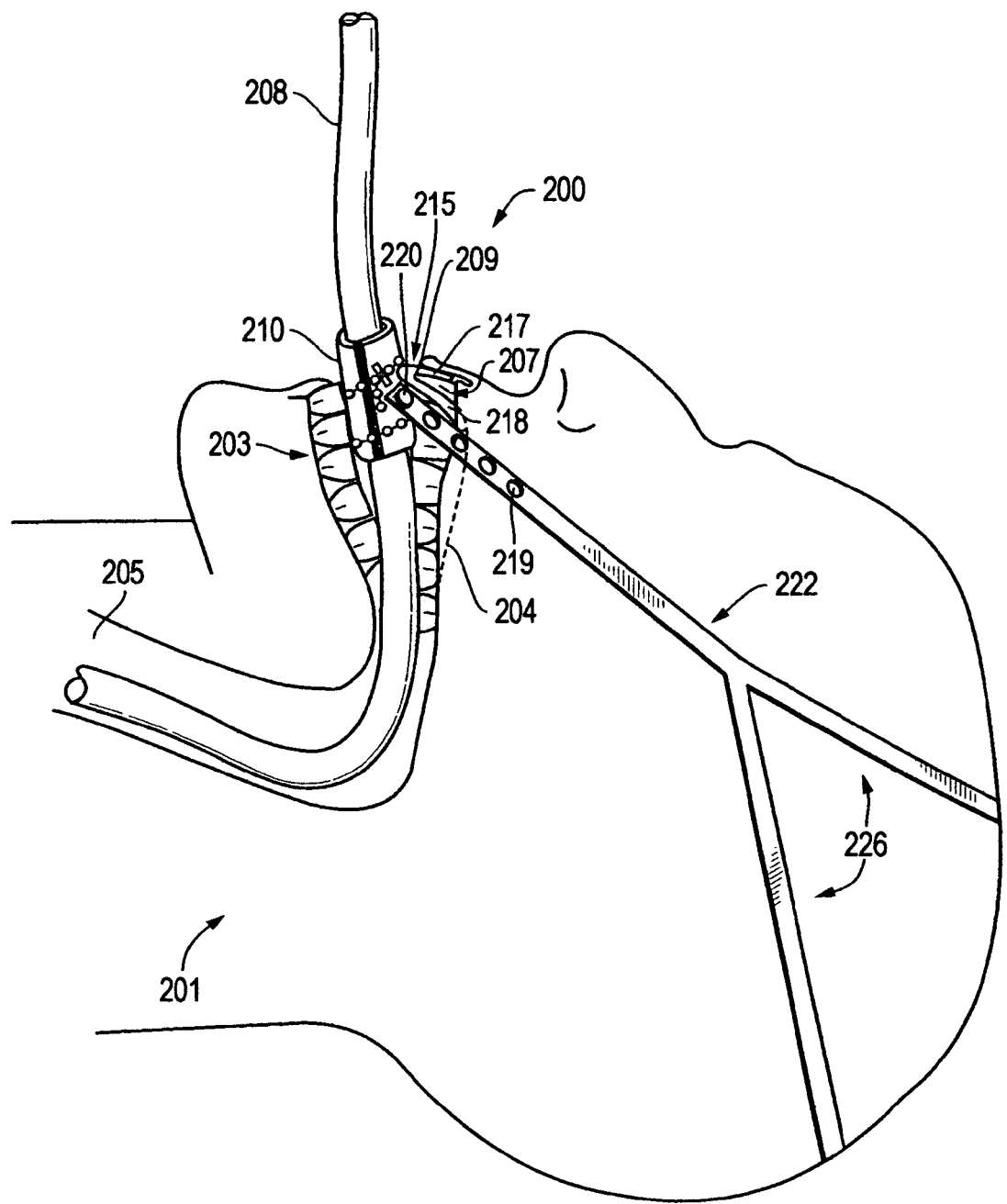
FIG. 7 is a partially cut-away, perspective view of an intubation system for attachment to a biteline of a patient's mouth, the intubation system includes an endotracheal tube and a tube holder assembly, the tube holder assembly including a bite support assembly and a bite tensioner assembly both coupled to a tube body, the bite tensioner assembly applies a tensile force to the tube body for enabling the bite support assembly to compress against the patient's biteline.
Figure 8:
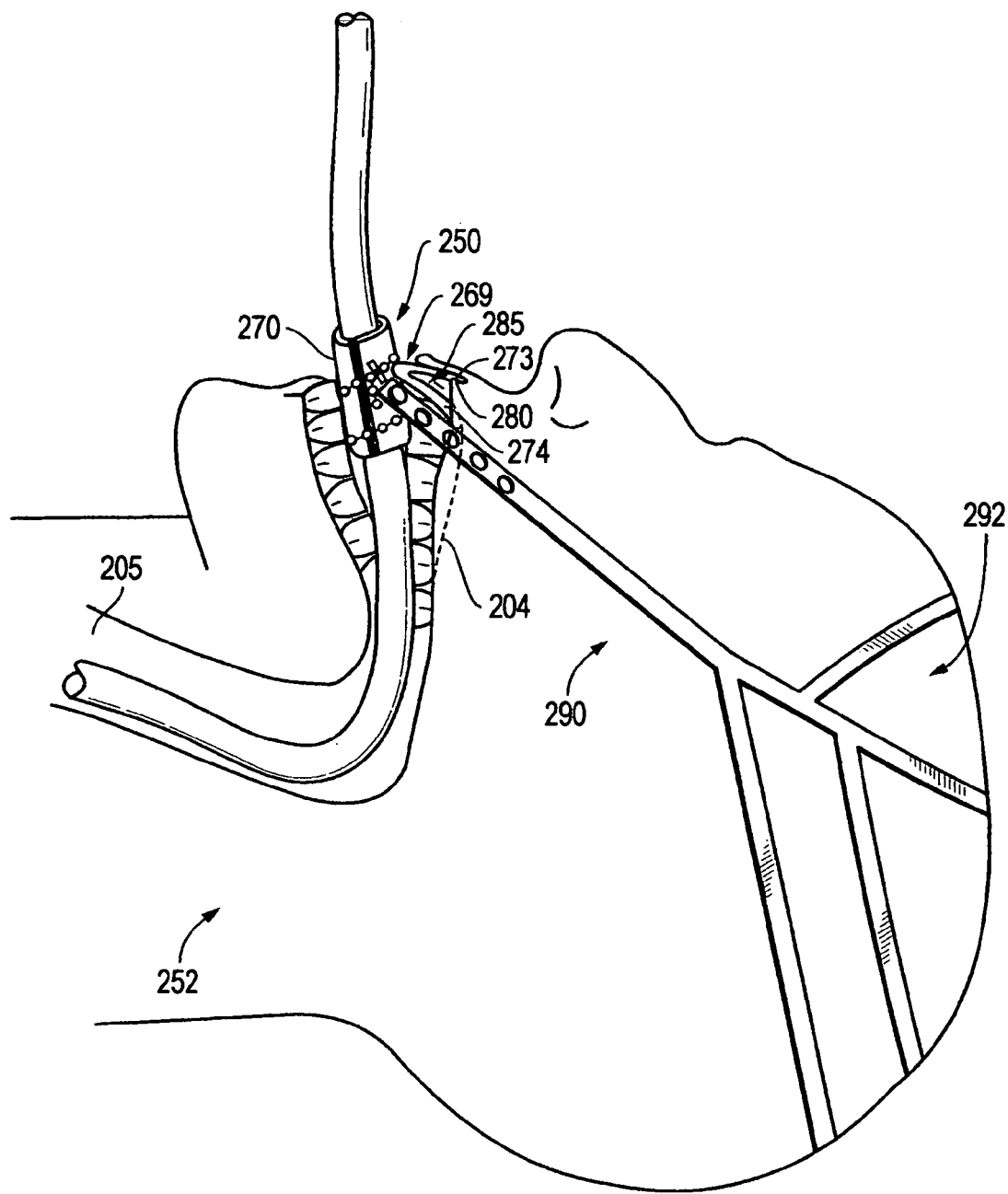
FIG. 8 is a partially cut-away, perspective view illustrating one exemplary embodiment of an intubation system for attachment to a biteline of a patient's mouth, the intubation system including a bite support assembly having a buccal side bite wall extending from the biteline and in contact with the attached gingival, and a lingual side bite wall extending from the biteline an din contact with the hard palate.

FIG. 1 illustrates one aspect, among others, of a tube holder assembly 10 for securing an endotracheal tube to a biteline of a patient's mouth. Generally, during a medical procedure, a tube holder assembly maintains a desired position of an endotracheal tube as it is firmly secured onto the biteline of a patient. Illustratively, FIGS. 7 and 8 show an intubation system for attachment to a biteline whereby a bite tensioner assembly applies a tensile force to a tube holder assembly for fixating the tube holder assembly against the biteline of a patient. In this disclosure and appended claims the term "biteline" refers to a row of teeth and including the peridontum of a patient's mouth in the absence of at least one tooth, whereby the term "patient" refers to either a human or an animal. Moreover, the endotracheal tube may comprise any endotracheal tube of a type well known in the industry, such as an endotracheal tube with or without an inflatable cuff as well as a dual bore endotracheal tube.

Specifically referring to FIG. 1, the tube holder assembly 10 includes a tube body 20. The tube body 20 features an exterior surface 21, an interior surface 25, and a pass-through slit 23 formed between exterior surface 21 and the interior surface 25.

In one exemplary embodiment, the tube body 20 is composed of a flexible, semirigid material such as a polymer. The tube body 20 must be sufficiently rigid so as to withstand compressive forces from the upper and lower jaws of a patient as the tube holder assembly 10 is operatively secured to the biteline.

Moreover, the tube body 20 is sufficiently flexible so as to hingedly receive and secure an endotracheal tube against the interior surface 25. FIG. 1 shows a hinge portion 22 defined by the tube body 20. The hinge portion 22 is located on the tube body 20 on the opposite side with respect to the pass through slit 23. Operatively, as the pass-through slit is either enlarged or narrowed, the hinge portion 22 exhibits flexure having characteristic hinge-like properties.

In one exemplary embodiment, the tube body 20 may optionally feature at least one retainment lip 27. Operatively, as it wedges against an endotracheal tube, a retainment lip prevents rotational slippage of an endotracheal tube with respect to an interior surface. Moreover, as an endotracheal tube is inserted within a tube body, an outward budge characteristic of the retainment lip assists in manually prying-open a pass-through slit.

The retainment lip 27 shown in FIG. 1 is located adjacent to the pass-through slit 23. As it extends along the length of the pass-through slit 23, the retainment lip 27 bulges outwardly from a plane that generally defines the interior surface 25.

In one exemplary embodiment, the tube body 20 may integrate sensors such as electrical or electrothermal sensors of a type well known in the industry for collecting biomedical data from a patient's mouth, such as for temperature reading or pulse. For example, at least one sensor may be coupled to the tube body 20 for engagement with a patient's mouth. Accordingly, in one exemplary embodiment, a power supply may be coupled to the tube body 20 to provide power to the sensor.

Figure 9:
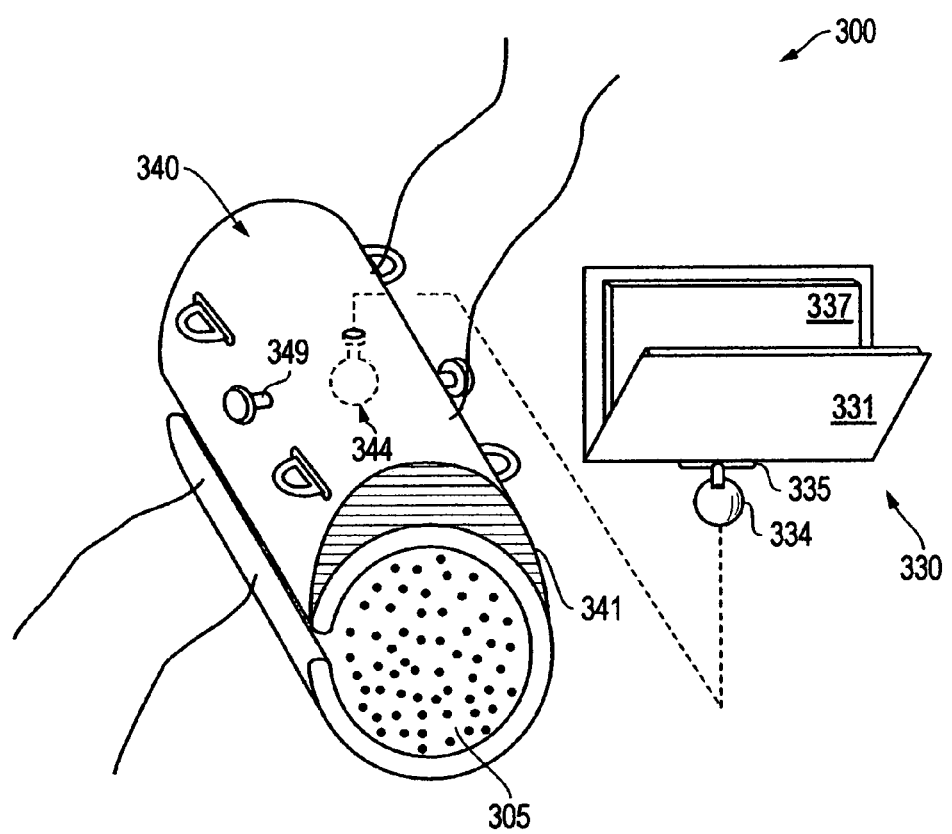
FIG. 9 is an exploded, isometric view illustrating one exemplary embodiment of a tube holder assembly, the tube holder assembly including a tube body and a bite support assembly pivotally coupled to the tube body via a ball joint coupling and socket chamber.

As shown in FIG. 1, an array of grip enhancers 29 are optionally provided about the interior surface 25 of the tube holder assembly 10. In operation, the array of grip enhancers 29 provide added surface area to the interior surface 25 for securing the endotracheal tube to the interior surface 25. Specifically, each grip enhancer extends outwardly from the interior surface 25 thereby providing added surface area for frictional contact against the endotracheal tube. Grip enhancers may assume a variety of shapes that are well known in the industry for providing frictional enhancement. For example, grip enhancers may assume a combination of different shapes such as pyramidal shapes as shown in FIG. 1, grooved shapes, hatched configurations, spherical shapes as shown in FIG. 5, rifled configurations as shown in FIG. 6, and gritted configurations as shown in FIG. 9.

Generally, the tube body 20 is compact in size to permit medical practitioners to access the entire mouth as need. In operation, illustratively for humans, a tube body may radially extend from 0.1 to 10.0 millimeters (mm.) outwardly from the endotracheal tube. Furthermore, the length of a tube body may range from 1 to 8 centimeters, (cm.).

The tube body 20 is dimensioned to securely receive an endotracheal tube, especially endotracheal tubes of varying sizes. In one exemplary embodiment, the size of the interior diameter of the tube body 20 may be configured to exactly accommodate the exterior diameter size of a corresponding endotracheal tube. Specifically, an exact accommodation may require that the entire outer diameter of the endotracheal tube circumferentially and continuously contacts the tube body's 20 interior surface 25 such that the pass-through slit 23 is entirely drawn together without any gap therebetween.

Illustratively, endotracheal tubes for humans fall within the inner diameter size range between 2.0 mm. and 10.0 mm. at 0.5 mm increments. Most human adults require an endotracheal tube inner diameter size between 6.0 mm. and 9.0 mm. To accommodate each particular outer diameter size of endotracheal tube, tube bodies may be provided at corresponding incremental inside diameter sizes. For example, an individual requiring a 7.5 mm. outer diameter endotracheal tube will receive a corresponding tube holder assembly from an array of available tube holder sizes having a tube body with an inside diameter slightly larger than 7.5 mm. and whereby the interior surface of the tube body circumferentially and continuously contacts the entire outer diameter of the endotracheal tube such that the pass through slit is drawn together and closed without a gap therebetween.

Although shown in FIG. 1 as cylindrical in shape, it should be added that a tube body in cross-section may encompass a variety of shapes including cylindrical, square, hexagonal, and octagonal configurations. Cross-sectional shapes are either varied or constant throughout the entire length of a tube body. Moreover, in one exemplary embodiment, a tube body may be bent at least in part along its length so as to ultimately affect the positioning of the endotracheal tube with respect to the patient.

In operation, an endotracheal tube is inserted within the tube holder assembly 10. Specifically, the endotracheal tube is inserted from the exterior surface 21 across the pass-through slit 23 to the interior surface 25, and is placed in circumferential contact with the interior surface 25. Alternatively, in one exemplary embodiment, the tube holder assembly 10 may be formed from one contiguous piece that does not feature a pass-through slit. Accordingly, one end of an endotracheal tube may be fed through one end of the tube holder assembly 10 without insertion across a pass-through slit.

The tube holder assembly 10 may further include a slit tensioning assembly 30. In operation, the slit tensioning assembly 30 applies a narrowing force to the pass-through slit 23 so that the interior surface 25 is compressively secured against the endotracheal tube.

As shown in FIG. 1, the slit tensioning assembly 30 includes at least one slit tensioning pull 33 and a corresponding slit tensioning anchor 31 for operative engagement with the slit tensioning pull 33. Each slit tensioning pull 33 and corresponding slit tensioning anchor 31 is secured to the exterior surface 21 at opposing locations relative to the pass-through slit 23.

Operatively, the slit tensioning pull 33 is drawn to close a gap defined by the pass-through slit 23. To ensure that the pass-through slit 23 remains closed, the slit tensioning anchor 31 locks the slit tensioning pull 33 in place. The slit tensioning pull 33 may be configured to include adjustable locking positions with respect to the slit tensioning anchor 31.

The slit tensioning pull 33 and anchor device 31 for the embodiment of FIG. 1 are of a type well known in the industry. It should be added that the slit tensioning assembly 30 of FIG. 1 may include a plurality of slit tensioning pulls and corresponding slit tensioning anchors to ensure that the endotracheal tube is locked in position with respect to the interior surface 25. Illustratively, the slit tensioning pull 33 may comprise a continuous cam array for ratcheting and, thus, locking to the slit tensioning anchor 31 as shown in FIG. 1. Alternatively, the slit tensioning pull 33 may comprise a cord having an array of beaded stoppers placed at a predetermined position whereby a desired stopper is secured to a corresponding slit tensioning anchor 31 comprising a locking rest.

In one exemplary embodiment, the tube holder assembly 10 may optionally provide at least one peripheral fastening assembly 35 coupled to the exterior surface 21 of the tube body 20. Generally, the peripheral fastening assembly 35 is configured for receiving at least one peripheral tube thereby coupling the at least one peripheral tube to the exterior surface 21. A peripheral tube may comprise any suitable tube of a type well known in the industry for use in conjunction with a tracheal intubation procedure. Illustratively, a peripheral tube may comprise a nasogastric tube, an orogastric tube, and esophageal thermometer. During intubation, as the tube holder assembly 10 secures an endotracheal tube to the biteline of a patient's mouth, other tubes such as a nasogastric tube may be secured to the exterior surface 21 of the tube holder assembly 10. Those of ordinary skill in the art will readily recognize any suitable means for securing a peripheral tube to the exterior surface 21 of a type well known in the industry such as hooks, loops, and a pull and corresponding anchor device similar to that of slit tensioning assembly 30.

The tube holder assembly 10 of FIG. 1 further includes a bite support assembly 40 coupled to the tube body 20. It should be said that in one exemplary embodiment the tube body 20 and the bite support assembly 40 are formed as one integral piece. Generally, the bite support assembly 40 receives a tensile force and supplies a compressive force to the mouth of a patient. In effect, the bite support assembly 40 clasps around the biteline and supplies a compressive force thereto so as to anchor the tube holder assembly 10 to the biteline.

Specifically, the bite support assembly 40 includes a pair of substantially parallel bite walls 44. In one exemplary embodiment, the bite support assembly 40 includes a pair of exactly parallel bite walls 44. The bite walls 44 extend outwardly from the exterior surface 21 of the tube body 20. As shown in FIG. 1, the bite walls 44 define a bite rest 45 in the space between the bite walls 44.

The bite rest 45 in operation receives the biteline of the patient's mouth thereby securing the biteline between each bite wall 44 as the bite rest 45 applies a compressive force to the biteline. Accordingly, the surface of biteline contact defined by a first bite wall, the bite rest, and an adjacent, second bite wall forms a trough-like configuration, such as either a U or V shape, for ensuring that the biteline is securely clamped therein. In one aspect, the separation between the first and second bite wall with respect to the bite rest forms a geometric angle in a range between 10° and 90°. In one exemplary embodiment, the bite support assembly 40 may comprise a tray that form fits onto the biteline.

As shown in FIG. 1, the tube holder assembly 10 further comprises a bite tensioner mount 47 coupled to the tube body 20. The bite tensioner mount 47 operatively receives a tensile force from a bite tensioner assembly coupled to the bite tensioner mount 47 as discussed in detail below.

Figure 2:
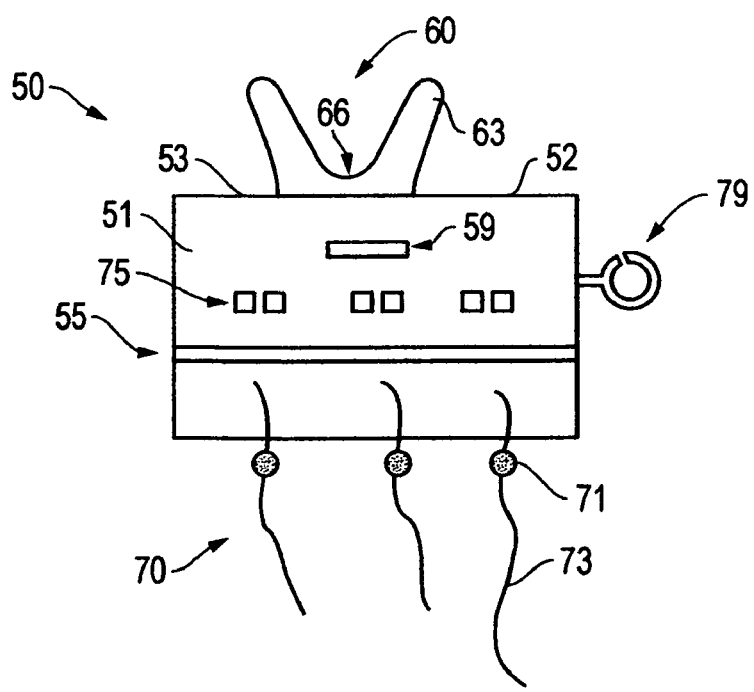
FIG. 2 is an orthographic view from the side illustrating one exemplary embodiment of a tube holder assembly; the tube holder assembly includes a pass-through slit for inserting an endotracheal tube therein and a slit tensioning assembly for narrowing the pass-through slit after insertion.

FIG. 2 illustrates one exemplary embodiment of a tube holder assembly 50. The tube holder 50 includes a tube body 51 having a front portion 52 and an opposing mouth portion 53. The tube holder assembly 50 further includes a bite support assembly 60 coupled to the tube body 50. Referring to the embodiment of FIG. 2, the length of the front portion 52 exposed outside of the mouth is relatively longer than the length of the mouth portion 53 operatively situated within the mouth. Accordingly, enhanced length of the front portion 52 exposed outside of the mouth permits medical practitioners to manually clamp along this area during standard intubation procedures such as securing the intubation tube within the tube holder.

For the embodiment of FIG. 2, the bite support assembly 60 is coupled at an offset position relative to the center of the tube body 51. As shown, the bite support assembly 60 is positioned toward the mouth portion 53 and away from the front portion 52. Accordingly, in operation, the front portion 52 provides sufficient room for manual contact of the tube holder assembly 50 during standard intubation procedures.

Illustratively, the tube holder assembly includes a slit tensioning assembly 70 for applying a narrowing force to a pass-through slit 75. Accordingly, a medical practitioner may manually clamp against the front portion 52 while manipulating the slit tensioning assembly 70 to lock the assembly 70 in place so that, ultimately, the tube body 51 is compressively secured against an endotracheal tube. Specifically, the slit tensioning assembly 70 features a slit tensioning pull 73 having a stop 71 that is drawn to rest against a corresponding slit tensioning anchor 75 as the front portion 52 receives a manual clamping force thereon.

The tube holder 50 also provides a peripheral fastening assembly 79 and is positioned on the front portion 52 for accommodating ease of manual access thereto. For example, for the embodiment of FIG. 2, the peripheral fastening assembly 79 comprises a hook for receiving and securing a peripheral tube such as a nasogastric tube to the front portion 52 of the tube holder assembly 50.

Referring to FIG. 2, the bite support assembly 60 includes a pair of bite walls 63 extending away from one another and outwardly from the tube body 51. The bite walls 63 define a bite rest 66 therebetween. The tube holder assembly 50 further includes a bite tensioner mount 59 coupled to the tube body 50 for receiving a tensile force and permitting the bite rest 66 to apply a compressive force to a biteline to thereby secure the tube holder assembly 50 to the biteline of a patient's mouth.

FIG. 3 is a side view illustrating one exemplary embodiment of a tube holder assembly 90 for securing an endotracheal tube to a biteline. The tube holder assembly 90 includes a tube body 91. The tube holder assembly 90 further includes a slit tensioning assembly 97, a bite tensioner mount 99, and a bite support assembly 100 each coupled to the tube body 91.

Specifically, the bite support assembly 100 includes a pair of bite walls 101 rendered in a symmetrically opposing configuration. Each bite wall 101 of FIG. 3 is of the same length. Each bite wall 101 is composed of a semirigid material so as to ultimately clasp around the biteline while maintaining complete structural integrity of the tube holder assembly 90. Optionally, in one exemplary embodiment, each bite wall 101 may be composed of a partially deformable, rigid material such as metal so as to ultimately form fit around the biteline as it is clasped thereon without compromising structural integrity of the tube holder assembly 90. As shown in FIG. 3, a cushioning element 103 is secured on to the bite support assembly 100 specifically from the distal end of one bite wall 101 across a bite rest 107, as defined between each bite wall 101, and to the distal end of the other bite wall 101. In effect, the cushioning element 103 protects the patient's biteline from trauma and provides comfort during extended periods of use. For example, the cushioning element may be composed at least in part of foam including memory foam, gel, and batting and other soft materials.

FIG. 4 is a side view illustrating one exemplary embodiment of tube holder assembly 110. The tube holder assembly 110 includes a tube body 111. The tube body 111 features a pass-through slit 114 formed along the length of the tube body 111 and a hinge portion opposedly located from the pass-through slit 114. Operatively, the hinge portion 113 facilitates the opening and closing of the pass-through slit 114 to accommodate the insertion of an endotracheal tube.

The tube holder assembly 110 further includes a bite support assembly 120 is coupled to an exterior surface 115 of the tube body 111. Moreover, as shown in the embodiment of FIG. 4, the bite support assembly situated at a predetermined bite deflection angle, α, that is measured from the normal axis to the radial plane defining the exterior surface 115. Those of ordinary skill in the art will readily recognize that the bite deflection angle α as any angle suitable for enabling the bite support assembly 120 to deliver the maximum amount of compressive force to the biteline. Illustratively, in one exemplary embodiment, the bite deflection angle α may be any acute angle relative to the normal axis of the exterior surface 115.

Referring to FIG. 4, the bite support assembly 120 includes a first bite wing 121 and a second bite wing 123 coupled to the first bite wing 121. The first bite wing 121 and the second bite wing 123 join together so as to form a bite rest 122 for receiving the biteline of a patient's mouth and, in operation, securing the pair of bite wings 121, 123 to the biteline as the bite rest 122 applies compressive force to the biteline. In one exemplary embodiment, the second bite wing 123 is characterized as having a relatively longer length as compared to the first bite wing 121. Operatively, the first bite wing 121 is situated on the biteline facing the lips of the patient's mouth whereas the second bite wing 123 is positioned entirely within the mouth from the biteline and extending outwardly along the length of a patient's hard palate.

Optionally, the bite support assembly 120 further includes a cushioning element 126 disposed along the bite support assembly 120 from the distal end of the first bite wing 121 across the bite rest 122 to the distal end of the second bite wall 123. The cushioning element 126 is provided for ergonomic support as the bite support assembly 120 is clasped to the biteline.

FIG. 5 is a top view illustrating one exemplary embodiment of a tube holder assembly 130. The tube holder assembly 130 includes a tube body 133 for securely receiving an endotracheal tube holder therein. The tube holder assembly 130 of FIG. 5 includes a bite tensioner mount 149 coupled to the tube body 133 for receiving a tensile force. In one exemplary embodiment, the bite tensioner mount 149 comprises a flanged element. Operatively, a bite support assembly 145 receives the tensile force from the bite tensioner mount 149 and supplies a compressive force to the mouth of the patient. Furthermore, FIG. 5 shows grip enhancers 137 for frictional engagement with an endotracheal tube placed circumferentially against the interior surface 135.

The tube holder assembly 130 further includes a slit tensioning assembly 146 for applying a narrowing force to the interior surface 135 to the interior surface so that the interior surface 135 is compressively secured against the endotracheal tube. Optionally, the tube holder assembly 130 may include at least one peripheral fastening assembly 140 for securing peripheral tubes to the tube body 133.

FIG. 6 is a bottom view illustrating one exemplary embodiment of a tube holder assembly 160. The tube holder assembly 160 includes a tube body 166 having an interior surface 167 and an exterior surface 170. Grip enhancers 169 are disposed on the interior surface 167 of the tube body 166 so as to ultimately secure the endotracheal tube against the interior surface 167. Specifically, in one exemplary embodiment, the grip enhancers are rendered in a rifled configuration whereby at least one spiraled grip enhancer is positioned about the interior surface 167.

The embodiment of FIG. 6 further includes bite groves 163 disposed along the exterior surface 170 defined by the tube body 166. Operatively, the bite groves 163 frictionally engage with teeth and tissues associated with the lower jaw such as the lower lip, peridontum, cheek, and tongue to ultimately prevent slippage by the tube holder assembly.

It should be added that a bite tensioner mount 177 is provided by the tube holder assembly 166. The bite tensioner mount 177 features a ring-like configuration.

FIG. 7 is a schematic diagram illustrating an intubation system 201 for attachment to a biteline 207 of a patient's mouth 203. The intubation system 201 includes an endotracheal tube 208. During standard intubation procedures, the endotracheal tube 208 is directed through the tracheal tube 205. The endotracheal tube 208 may be an endotracheal tube of a type well known in the industry. Moreover, an endotracheal tube may be selected from an array of predetermined diameter sizes.

The intubation system 201 further includes a tube holder assembly 200 coupled to the endotracheal tube 208. The tube holder assembly 200 includes a tube body 210. The tube body 210 includes an exterior surface, an interior surface, and a pass-through slit extending along the length of the tube body 210. Operatively, the endotracheal tube 208 is inserted from the exterior surface, across the pass-through silt to the interior surface for operative contact with the interior surface as shown in FIG. 7.

The tube holder assembly 200 further includes a bite tensioner assembly 222 and a bite tensioner mount 220 coupled to the tube body 210. In operation, the bite tensioner assembly 222 applies a tensile force to the bite tensioner mount 220. As shown in FIG. 7, the bite tensioner assembly 222 features two opposing ends having a tensioner lock 219 and anchor webbing 226 at another end. The tensioner lock 219 is secured to the bite tensioner mount 220. The anchor webbing 226 is fixed to the patient's body such that the tensile force is exerted along the bite tensioner assembly 222 from the tensioner lock 219 at the bite tensioner mount 220 to the anchor webbing 226. Optionally, an array of tensioner locks may be applied on the bite tensioner assembly 222 for variable adjustment according to the body size of the patient as well as the degree of tensile force desired for engagement with a bite tensioner mount 220.

Illustratively, as shown in FIG. 7, the anchor webbing 226 is secured about the frontal and parietal regions of the patient's skull. Securing the anchor webbing 226 can be achieved by a single medical practitioner. Moreover, in one exemplary embodiment, the bite tensioner assembly 222 is composed of a resilient material such that the anchor webbing 226 is stretched over the skull that consequently exerts a tensile force at the tensioner lock 219. In one exemplary embodiment, the tensioner assembly includes a belt buckle assembly (not shown) having a belt buckle for drawing a tension on the bite tensioner assembly 222 from the tensioner lock 220 to anchor webbing 226.

The tube holder assembly 200 further includes a bite support assembly 215 coupled to the tube body 210. Operatively, the bite support assembly 215 receives the tensile force from the bite tensioner mount 220 and supplies a compressive force to the mouth 203 of a patient. Specifically, the bite support assembly 215 includes a pair of substantially parallel bite walls 217–18 extending outwardly from the exterior surface of the tube body 210.

Generally, the bite walls define a bite rest for receiving the biteline 207 thereby securing the biteline 207 between the pair of bite walls 217–18 as the bite rest applies a compressive force to the biteline 207. Securing both the bite support assembly 215 and the anchor webbing 226 can be achieved by a single medical practitioner.

Figure 7A:
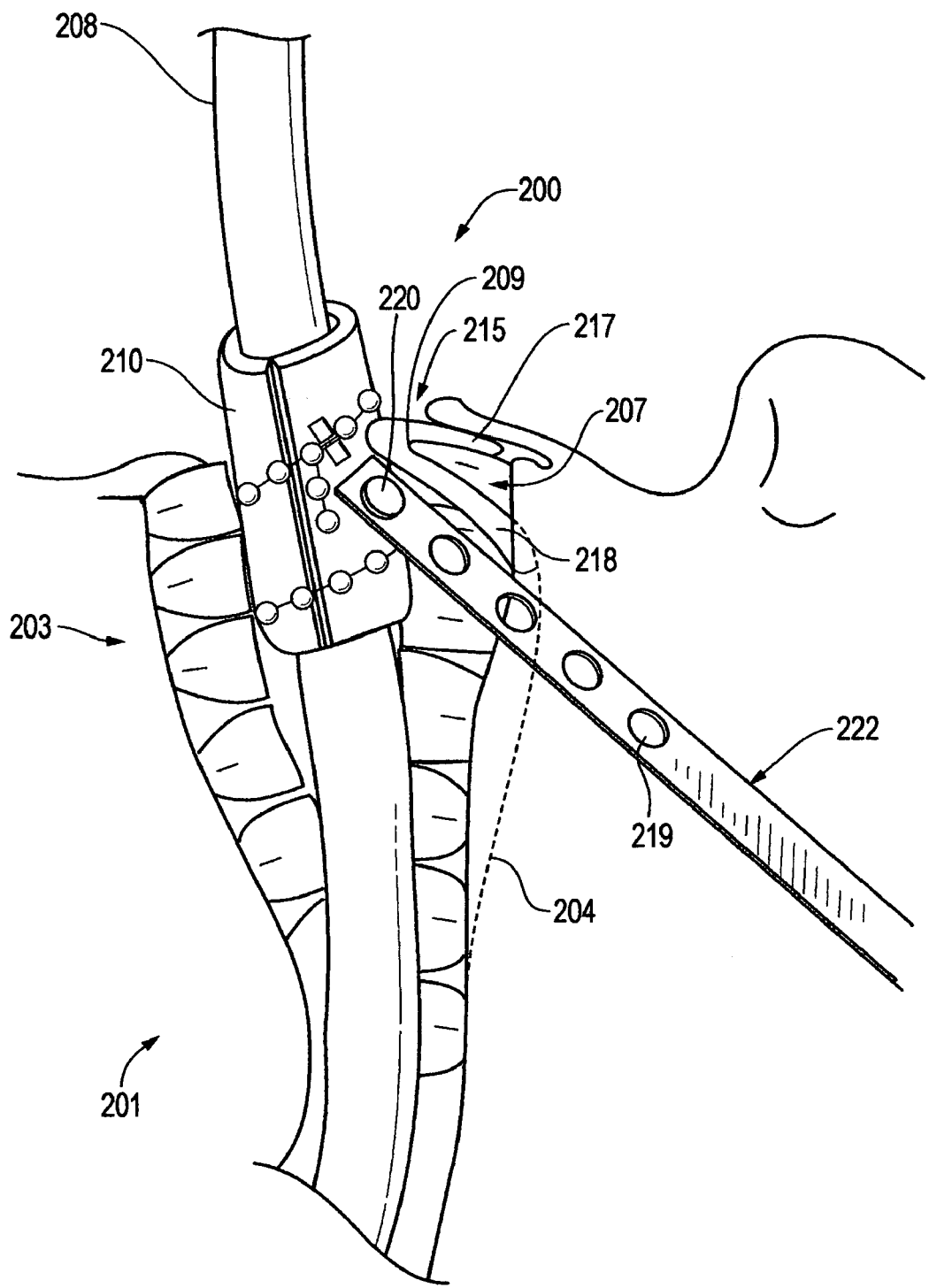
FIG. 7a is a detailed view of the intubation system of FIG. 7.

As specifically shown in FIG. 7a, the bite support assembly 215 includes a frontal bite wall 217 operatively positioned between the patient's lip and biteline. The bite support assembly 215 further includes a rearward bite wall 218 coupled to the frontal bite wall 217. The rearward bite wall 218 is positioned within the mouth 203 and rests against the biteline 207 and extends across the hard palate 204 of the patient 207.

Specifically referring to FIG. 7, the tube holder assembly further includes a bite tensioner mount coupled to the tube body 210. In operation, the bite tensioner assembly applies a tensile force to the bite tensioner mount coupled to the tube body.

Generally, FIGS. 7 and 8 illustrate at least one method for intubating a patient. For example, referring to FIG. 7, an endotracheal tube is inserted within a tube holder assembly. The endotracheal tube is passed through an interior surface of the tube body as it is ultimately directed through the patient's trachea 205. The tube holder assembly is secured onto a biteline 207 of the patient's mouth.

In one exemplary method, the tube holder assembly further includes a bite support assembly coupled to the tube body. The bite support assembly receives a tensile force from a bite tensioner mount. Accordingly, the bite support assembly, supplies a compressive force to the mouth of the patient. Optionally, in one exemplary embodiment, the bite support assembly includes a ball joint coupling for ultimately pivoting the tube holder assembly with respect to the biteline.

As the endotracheal tube is placed in a desired position with respect to the trachea 205, the endotracheal tube is locked in place via the tube holder assembly. In particular, the tube holder assembly further includes a slit tensioning assembly. Operatively, the slit tensioning assembly narrows the pass through slit so that the interior surface is compressively secured against the endotracheal tube.

The bite tensioner assembly anchors the tube holder assembly to the patient's head to ensure a fixed, stable attachment of the bite support assembly to the biteline as a patient is generally lying at rest during a tracheal intubation procedure. Accordingly, the bite tensioner assembly is positioned on the patient's head in an area that is easily accessible and typically free of the patient's skin, muscle or joint movement.

As illustrated in FIGS. 7 and 8, the anchor webbing may assume a variety of configurations for ultimately securing the tube holder assembly to the biteline. For example, in FIG. 7, the bite tensioner assembly is secured to the parietal and/or frontal regions of the patient's skull. Illustratively, the parietal region is a non-obstructive location for most procedures involving tracheal intubation and provides little biomechanical movement as a tensile force is drawn across the bite tensioner assembly and applied to the tube holder assembly.

FIG. 8 is a perspective view illustrating one exemplary embodiment of an intubation system 252. The intubation system 252 includes a tube holder assembly 250 having a bite support assembly 269 coupled to a tube body 270. The bite support assembly 269 includes a pair of bite walls, specifically a buccal side bite wall 273 and a lingual side bite wall 274. "Buccal" refers to the area of the mouth near the lips and cheeks that is anterior to the teeth and gums whereas "lingual" refers to the area of the mouth posterior to the teeth and gums within the mouth cavity including the hard palate and tongue.

Figure 8A:
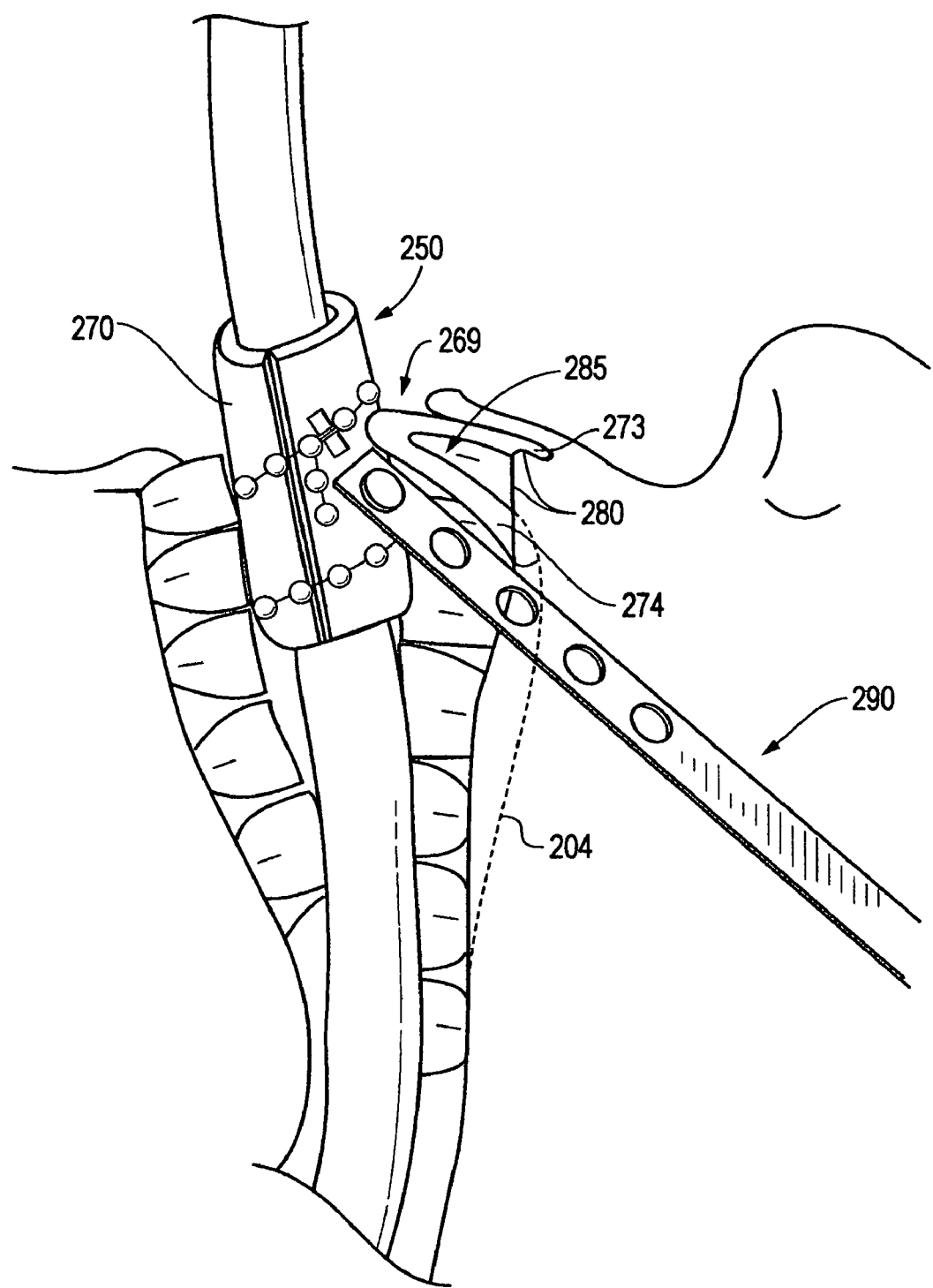
FIG. 8a is a detailed view of the intubation system of FIG. 8.

As shown in FIG. 8, the lingual side bite wall 274 extends from a bite line 285 outwardly against the hard palate. As shown in FIG. 8a, the buccal side bite wall 273 extends from the biteline and contacts against the attached gingiva. It should be added that the biteline of FIG. 8 includes teeth and peridontum whereby the bite support assembly clamps against all or a portion of the teeth and optionally the gingiva. Accordingly, the buccal side bite wall 274 extends across the teeth and gum line to ultimately enhance overall support of the tube holders 250. The anchor webbing 292 is shown in FIG. 8 to extend against both the frontal and parietal regions of the skull for increased fixation to the patient.

FIG. 9 is an exploded view illustrating one exemplary embodiment of a tube holder assembly 300 for pivotal attachment to a biteline. In general, the tube holder assembly 300 is similar to the tube holder assemblies referenced in FIGS. 1 through 8. The tube holder assembly 300 includes a tube body 340 having an interior surface. The tube body 340 of FIG. 9 features a spacer region 341 formed above the interior surface 340. The spacer region 341 defines a socket chamber 344 therein.

The tube holder assembly 300 further includes a bite support assembly 330 pivotally coupled to the tube body 340. The bite support assembly 330 includes a pair of substantially parallel bite walls 331. As shown in FIG. 9, the pair of bite walls 331 are mounted to and joined together by a bite wall coupling mount 335. Optionally, a cushioning element 337 may be coupled to the bite walls 331.

A ball joint coupling 334 is secured to and extends from the bite coupling mount 335. The ball joint coupling 334 is set at least in part within the socket chamber 334. In effect, the ball joint coupling 334 slides about the socket chamber 344, thereby pivotally coupling the bite support assembly 330 to the tube body 340. Those of ordinary skill in the art will readily recognize that tolerance between the ball joint coupling 334 and the socket chamber 344 may provide a range between loose and tight pivotal adjustment.

In one exemplary embodiment, as shown in FIG. 9, the tube body 340 includes a bite tensioner mount 349 coupled to the tube body 340 for receiving a tensile force from a bite tensioner assembly (not shown). Operatively, the pivotal coupling between the bite support assembly 330 and the tube body 340 enables the bite tensioner mount to position the tube body 340 from side-to-side or up and down as the bite tensioner assembly is situated on to the patient.

Alternatively, a bite tensioner mount may be coupled to the bite support assembly 330. In particular, the bite tensioner mount may be secured to the bite wall coupling 335. In one exemplary embodiment, the bite tensioner mount may extend outwardly from the bite wall coupling mount 335 and from the bite walls 331 so as not to interfere with operation of the bite walls 331. The bite tensioner mount receives a tensile force from the bite tensioner assembly to thus secure the bite support assembly 330 to a biteline. As the support assembly 330 is secured to the biteline, the ball joint coupling 334 and socket chamber 344 permit the tube body 340 and ultimately the endotracheal tube to be pivotally adjusted during intubation independently from the fixated bite support assembly.

Generally, FIGS. 10 through 14 illustrate some configurations, among others, of at least one bite wall with respect to a holding tube. In effect, the bite walls shown in FIGS. 10–14 are configured to conform to the biomechanical features associated with the biteline to effectively clamp thereon for up to long periods within the mouth. Those of ordinary skill in the art will readily recognize other suitable configurations for each bite wall so as to effectively affectively engage with a patient's biteline.

Figure 10:
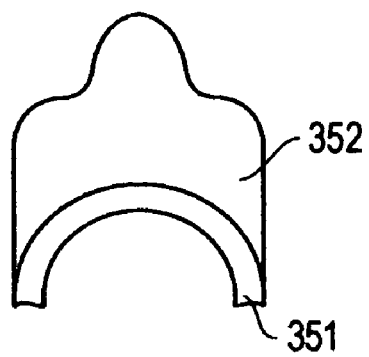
FIG. 10 is an orthographic view from one end illustrating one exemplary embodiment of a bite wall coupled to a holding tube.

FIG. 10 shows at least one bite wall 352 coupled to a holding tube 351. The bite wall 352 includes an outwardly extending tab portion. The outwardly extending tab portion is provided for increased contact surface area with the region associated with the biteline.

Figure 11:
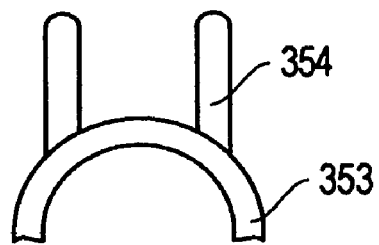
FIG. 11 is an orthographic view from one end illustrating one exemplary embodiment of a bite wall coupled to a holding tube.

FIG. 11 shows at least one bite wall 354 coupled to a holding tube 353. The bite wall 354 features a plurality of elongated members for contact with area associated with the biteline. For example, the bite wall 354 may be used to clamp against teeth on either side of a gap created by a missing tooth or teeth.

Figure 12:
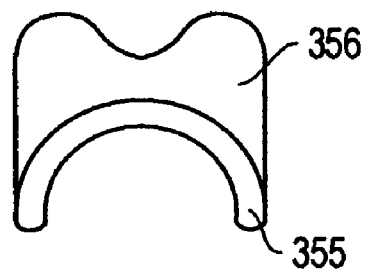
FIG. 12 is an orthographic view from one end illustrating one exemplary embodiment of a bite wall coupled to a holding tube.

FIG. 12 illustrates at least one bite wall 356 coupled to a holding tube 355. The bite wall 356 features a plurality of outwardly extending tab portions. Each tab provides increased contact surface area with the region associated with the biteline.

Figure 13:
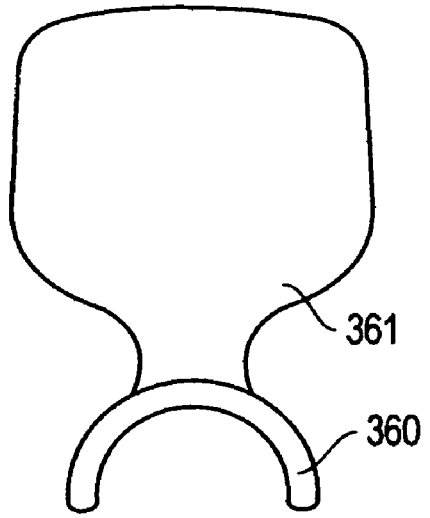
FIG. 13 is an orthographic view from one end illustrating one exemplary embodiment of a bite wall coupled to a holding tube.

FIG. 13 illustrates a tube body 360 coupled to bite wall 361. The bite wall 361 is configured to sufficiently conform to the basic contours associated with the hard palate.

Figure 14:
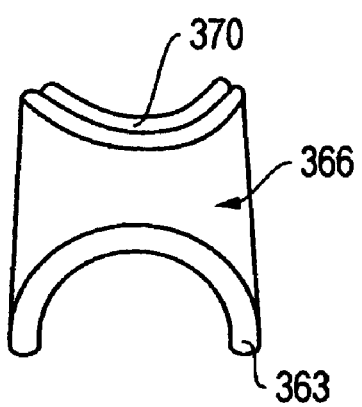
FIG. 14 is an isometric view from one end illustrating one exemplary embodiment of a bite support assembly coupled to a holding tube.

FIG. 14 illustrates a holding tube 363 coupled to a bite support assembly 366. The bite support assembly 366 features at least one bite wall 370. The at least one bite wall 370 is curved so as to directly conform to the contours associated with the biteline.

Although the present invention has been described in detail, it should be understood that various changes, substitutions, and alterations could be made hereto without departing from the spirit and scope of the invention as defined by the appended claims.

I claim:

1. A tube holder assembly for securing an endotracheal tube to a biteline of a patient's mouth via a tensile force, the tube holder assembly comprising:
   a tube body,
      the tube body including an exterior surface and an interior surface, the endotracheal tube received by the tube body and is placed in circumferential contact against the interior surface;
   a bite tensioner mount coupled to the tube body and receiving the tensile force; and
   a bite support assembly coupled to the tube body,
      the bite support assembly receiving the tensile force from the bite tensioner mount and supplying a compressive force to the mouth of the patient,
      the bite support assembly including a pair of substantially parallel bite walls extending outwardly from the exterior surface of the tube body,
      the bite walls defining a bite rest therebetween, the bite rest receiving the biteline of the patient's mouth thereby securing the biteline between the pair of bite walls as the bite rest applies the compressive force to the biteline.

2. The tube holder assembly according to claim 1 wherein the tube body further includes a pass-through slit extending along the length of the tube body.

3. The tube holder assembly according to claim 1 wherein the endotracheal tube is inserted from the exterior surface across the pass-through slit to the interior surface and is placed in circumferential contact against the interior surface.

4. The tube holder assembly according to claim 1 further comprising a bite tensioner assembly for applying the tensile force to the bite tensioner mount.

5. The tube holder assembly according to claim 1 wherein the bite tensioner assembly includes two opposing ends and wherein one end includes a tensioner lock and another end includes anchor webbing.

6. The tube holder assembly according to claim 1 wherein the tensioner lock is secured to the tensioner mount of the tube body and the anchor webbing is fixed to the patient, the tensile force is exerted along the bite tensioner assembly from the tensioner lock to the anchor webbing.

7. The tube holder assembly according to claim 1 wherein the bite tensioner assembly is composed of a resilient material.

8. The tube holder assembly according to claim 1 further comprising a slit tensioning assembly, the slit tensioning assembly applies a narrowing force to the pass-through slit, the narrowing force compressively secures the interior surface against the endotracheal tube.

9. The tube holder assembly according to claim 1 wherein the slit tensioning assembly includes a slit tensioning pull and a slit tensioning anchor, each secured to the exterior surface at opposing locations relative to the pass-through slit.

10. The tube holder assembly according to claim 1 further comprising a peripheral fastening assembly coupled to the exterior surface, the peripheral fastening assembly configured for receiving at least one peripheral tube thereby coupling the at least one peripheral tube to the exterior surface of the tube body.

11. The tube holder assembly according to claim 1 wherein the tube body is composed of a flexible, semirigid material.

12. The tube holder assembly according to claim 1 wherein the tube body and bite support assembly form one integral piece.

13. The tube holder assembly according to claim 1 wherein the bite support assembly is pivotally coupled to the tube body.

14. A tube holder assembly for securing an endotracheal tube to a biteline of a patient's mouth, the tube holder assembly comprising:
   a tube body,
      the tube body including an exterior surface, an interior surface, and a pass-through slit extending along the length of the tube body, the endotracheal tube is applied from the exterior surface across the pass-through slit to the interior surface and is placed in circumferential contact against the interior surface;
   a bite tensioner mount coupled to the tube body;
   a bite tensioner assembly for applying a tensile force to the bite tensioner mount,
      the bite tensioner assembly including a tensioner lock secured to the bite tensioner mount and anchor webbing fixed to the patient so that the tensile force is exerted along the bite tensioner assembly from the tensioner lock to the anchor webbing; and
   a bite support assembly coupled to the tube body,
      the bite support assembly receiving the tensile force from the bite tensioner mount and supplying a compressive force to the mouth of the patient,
      the bite support assembly including a pair of substantially parallel bite walls extending outwardly from the exterior surface of the tube body, the bite walls defining a bite rest therebetween, the bite rest receiving the biteline of the patient's mouth thereby securing the biteline between the pair of bite walls as the bite rest applies the compressive force to the biteline.

15. A method for intubating a patient comprising the steps of:
inserting an endotracheal tube within a tube holder assembly,
the tube holder assembly including a tube body having an exterior surface, an interior surface, and a pass-through slit extending along the length of the tube body;
passing the endotracheal tube through the patient's trachea, the endotracheal tube passing through the interior surface of the tube body;
securing the tube holder assembly to a biteline of the patient's mouth,
the tube holder assembly further including a bite support assembly coupled to the tube body,
the bite support assembly receiving the tensile force from a bite tensioner mount and supplying a compressive force to the mouth of the patient,
the bite support assembly including a pair of substantially parallel bite walls extending outwardly from the exterior surface of the tube body,
the bite walls defining a bite rest therebetween, the bite rest receiving the biteline of the patient's mouth thereby securing the biteline between the pair of bite walls as the bite rest applies the compressive force to the biteline;
locking the endotracheal tube in place via the tube holder assembly,
the tube holder assembly further including a slit tensioning assembly for operatively narrowing the pass-through slit so that the interior surface is compressively secured against the endotracheal tube; and
anchoring the tube holder assembly to the patient's head,
the tube holder assembly further including a bite tensioner mount coupled to the tube body and a bite tensioner assembly for applying a tensile force to the bite tensioner mount, the bite tensioner assembly including a tensioner lock secured to the bite tensioner mount and anchor webbing fixed to the patient's head so that the tensile force is applied along the bite tensioner assembly from the tensioner lock to the anchor webbing.

16. The method according to claim 15 wherein the step of inserting the endotracheal tube within a tube holder assembly further comprises the step of directing the endotracheal tube from the exterior surface across the pass-through slit to the interior surface for placement in circumferential contact against the interior surface.

17. The method according to claim 15 wherein the step of securing the tube holder assembly to the biteline of the patient's mouth further comprises the step of pivoting the tube holder assembly with respect to the biteline via the bite support assembly, the bite support assembly including a ball-joint coupling.

18. The method according to claim 15 further comprising the step of coupling a peripheral tube to the tube holder assembly, the tube holder assembly including a peripheral fastening assembly coupled to the exterior surface, the peripheral fastening assembly configured for receiving at least one peripheral tube thereby coupling the at least one peripheral tube to the exterior surface of the tube body.

* * * * *